(12) United States Patent
Kim et al.

(10) Patent No.: US 10,488,924 B2
(45) Date of Patent: Nov. 26, 2019

(54) WEARABLE DEVICE, AND METHOD OF INPUTTING INFORMATION USING THE SAME

(71) Applicant: KOREA ELECTRONICS TECHNOLOGY INSTITUTE, Seongnam-si, Gyeonggi-do (KR)

(72) Inventors: Kun Nyun Kim, Yongin-si (KR); Kwang Bum Park, Yongin-si (KR); Yeon Hwa Kwak, Seoul (KR); Won Hyo Kim, Yongin-si (KR)

(73) Assignee: KOREA ELECTRONICS TECHNOLOGY INSTITUTE, Seongnam-si, Gyeonggi-Do (KR)

(*) Notice: Subject to any disclaimer, the term of this patent is extended or adjusted under 35 U.S.C. 154(b) by 0 days.

(21) Appl. No.: 15/537,679

(22) PCT Filed: Dec. 1, 2015

(86) PCT No.: PCT/KR2015/012969
§ 371 (c)(1),
(2) Date: Jun. 19, 2017

(87) PCT Pub. No.: WO2016/099049
PCT Pub. Date: Jun. 23, 2016

(65) Prior Publication Data
US 2018/0011536 A1 Jan. 11, 2018

Related U.S. Application Data

(63) Continuation-in-part of application No. PCT/KR2015/007468, filed on Jul. 17, 2015.

(30) Foreign Application Priority Data

Dec. 17, 2014 (KR) .................. 10-2014-0181985

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/6824* (2013.01); *G06F 1/163* (2013.01); *G06F 3/017* (2013.01);
(Continued)

(58) Field of Classification Search
CPC ......... A61B 5/11; A61B 5/681; A61B 5/6824; A61B 5/721; G06F 1/163;
(Continued)

(56) References Cited

U.S. PATENT DOCUMENTS 6,640,202 B1 * 10/2003 Dietz ...................... A41H 1/02
342/118
2003/0173408 A1 9/2003 Mosher, Jr. et al.
(Continued)

FOREIGN PATENT DOCUMENTS

KR 10-2004-0089728 A 10/2004
KR 10-2010-0076136 A 7/2010
(Continued)

OTHER PUBLICATIONS

International Search Report for PCT/KR2015/012969 dated Apr. 1, 2016 from Korean Intellectual Property Office.

*Primary Examiner* — Sanjiv D. Patel
(74) *Attorney, Agent, or Firm* — Paratus Law Group, PLLC

(57) ABSTRACT

Disclosed is a wearable device including a sensor array having a plurality of sensors each configured to detect a physical change in epidermis of a corresponding body area; and a body motion determination unit configured to determine movement of a body part based on sensing signals
(Continued)

from the plurality of sensors, and determine whether the determined movement corresponds to one of at least one next motion which is able to be derived from a current motion state.

9 Claims, 10 Drawing Sheets

(51) Int. Cl.
  *G06F 1/16* (2006.01)
  *G06F 3/0346* (2013.01)

(52) U.S. Cl.
  CPC .... *G06F 3/0346* (2013.01); *A61B 2562/0247* (2013.01)

(58) Field of Classification Search
  CPC ........... G06F 2203/04105; G06F 3/011; G06F 3/017; G06F 3/0346; G06F 21/32; G06F 3/014; G06F 2203/013; G06F 2203/015; G06F 3/016
  See application file for complete search history.

(56) References Cited

U.S. PATENT DOCUMENTS

| | | | |
|---|---|---|---|
| 2004/0106881 A1* | 6/2004 | McBean | A61B 5/04888 601/5 |
| 2009/0293631 A1* | 12/2009 | Radivojevic | G01L 1/16 73/774 |
| 2009/0326833 A1* | 12/2009 | Ryhanen | G06F 3/014 702/33 |
| 2010/0245078 A1 | 9/2010 | Nadkarni et al. | |
| 2010/0259472 A1* | 10/2010 | Radivojevic | G06F 3/014 345/156 |
| 2011/0054360 A1* | 3/2011 | Son | A61B 5/1126 600/595 |
| 2012/0157886 A1* | 6/2012 | Tenn | A61B 5/04888 600/595 |
| 2014/0028546 A1* | 1/2014 | Jeon | G06F 3/014 345/156 |
| 2016/0299570 A1* | 10/2016 | Davydov | G06F 1/163 |
| 2017/0045946 A1* | 2/2017 | Smoot | G06F 3/017 |

FOREIGN PATENT DOCUMENTS

| | | |
|---|---|---|
| KR | 10-2011-0022520 A | 3/2011 |
| KR | 10-2014-0013845 A | 2/2014 |

* cited by examiner (BEFORE GRABBING MOVENENT)

(AFTER GRABBING MOVENENT)

(BEFORE TWISTING WRIST)

(AFTER TWISTING WRIST)

(BEFORE SPREADING FINGERS)

(AFTER SPREADING FINGERS)

(BEFORE MOVING WRIST DOWNWARD)
- WHEN WRIST IS BENT UPWARD (AFTER MOVING WRIST DOWNWARD)

WEARABLE DEVICE, AND METHOD OF INPUTTING INFORMATION USING THE SAME

CROSS REFERENCE TO PRIOR APPLICATIONS

This application is a National Stage Patent Application of PCT International Patent Application No. PCT/KR2015/012969 (filed on Dec. 1, 2015) under 35 U.S.C. § 371, which claims priority to PCT International Patent Application No. PCT/KR2015/007468 (filed on Jul. 17, 2015), and Korean Patent Application No. 10-2014-0181985 (filed on Dec. 17, 2014), which are all hereby incorporated by reference in their entirety.

BACKGROUND OF THE INVENTION

Field of the Invention

The present invention relates to a wearable device and a method of inputting information using the same, and more particularly, to a wearable device capable of detecting a current or next movement of a device wearing user to operate an external device, and a method of controlling operations of the device.

Related Art

As computer environments have become ubiquitous, various types of information inputting device have been developed. The change in a technique of the information inputting device is evolving from a portable keyboard into a wearable device, which is an information inputting device using a body part. The wearable device indicates any device able to be attached to a human body and perform computing, and such a wearable device includes even an application capable of performing a computing function.

Korean Patent Application Publication No. 10-2010-0076136 relates to an apparatus for recognizing biometric information, the apparatus which is in the form of a sensor bracelet to be worn around and which is capable of measuring electrocardiogram data, a pulse wave, and body temperature. The apparatus is a wearable device whose shape is different from a conventional shape, and which obtains an electrical signal of a human body from a sensor at predetermined intervals and stores and processes the signal by use of an MCU. With a semi-active sensor tag technology (hardware, firmware), it is possible to process the signal into medical information.

Korean Patent Application Publication No. 10-2004-0089728 relates to an identification appliance for providing personal information, the appliance which can be worn by or attached to a person to obtain the person's information, such as the person's finger print, retina, iris, blood, DNA, generic data, voice pattern, temperature, and other characteristics. In addition, the application can be used to monitor locations of passengers in an airplane, a train, a boat, a bus, or any other vehicle or to identify the passengers.

SUMMARY OF THE INVENTION

One embodiment of the present invention is to provide an apparatus that detects a physical change in human body epidermis so as to recognize movement of a body part and input information based on the movement.

One embodiment of the present invention is to provide an apparatus of inputting information, the apparatus which detects a physical change in wrist epidermis, which is caused by a change in wrist muscles, so as to recognize movement of a finger and a wrist.

One embodiment of the present invention is to provide a method of inputting information to control an external device based on recognized movement of a body part.

One embodiment of the present invention is to provide a wearable device that detects a physical change in human body epidermis so as to detect the current motion and a next motion and control an external device based on the current motion and the next motion.

One embodiment of the present invention is to provide a wearable device that detects a physical change in wrist epidermis, which is caused by a change in wrist muscles, so as to detect the current and next motions of a finger and a wrist.

In embodiments of the present invention, a wearable device includes: a sensor array having a plurality of sensors each configured to detect a physical change in epidermis of a corresponding body area; and a body motion determination unit configured to determine movement of a body part based on sensing signals from the plurality of sensors, and determine whether the determined movement corresponds to one of at least one next motion which is able to be derived from a current motion state.

The sensor array may be positioned in a wrist to detect a physical change in wrist epidermis, which is caused by a change in muscles including flexor hallucis longus and flexor digitorum profundus.

A density of the plurality of sensors may be proportional to a density of muscles underneath the epidermis of the corresponding body area.

When the corresponding body part is a wrist, a density of the plurality of sensors in intrinsic muscles of the wrist may be different from a density of the plurality of sensors in extrinsic muscles of the wrist.

The wearable device may further include a body movement pattern storage configured to store pre-defined sensing signal patterns of the plurality of sensors in association with movements of the body part.

The body motion determination unit may detect a similarity level by comparing information on the received sensing signals and the sensing signal patterns stored in the body movement pattern storage, and determine movement of the body part based on the similarity level.

The wearable device may further include a motion state management unit a moment state table that comprises at least one momentary motion state and transition of the at least one momentary motion state.

The motion state management unit may store the motion state table in association with information about operations of an external device corresponding to the motion state table.

The wearable device may further include a motion state determination unit configured to detect a current motion, and, based on the motion state table, determine at least one next motion state which is able to be transitioned from a current motion state associated with the detected current motion.

When the current motion state is not included in the motion state table, the motion state determination unit may detect a current motion again.

The body movement determination unit may detect a next motion based on the current motion, and check whether the detected next motion matches at least one next motion state determined by the motion state determination unit.

When the detected next motion does not match the at least one next motion state determined by the motion state determination unit, the body movement determination unit may detect a next motion again.

The wearable device may further include a communication unit configured to, when the detected next motion matches the at least one next motion state determined by the motion state determination unit, transmit, via the motion state management unit, information about operations of an external device, the information which is associated with the motion state table.

The wearable device may further include an inertial sensor configured to measure an angular velocity and acceleration and positioned in proximity to an epidermal region underneath the corresponding body area, the region in which a density of muscles is equal to or less than a specific reference value.

The body movement determination unit may determine movement of the body part based on the angular velocity and acceleration measured by the inertial sensor along with the sensing signals from the plurality of sensors.

In embodiments of the present invention, a method of inputting information includes: detecting a physical change in epidermis of a corresponding body area from a sensor array having a plurality of sensors; and at a body movement determination unit, determining movement of a body part based on sensing signals received from the plurality of sensors, and determining whether the determined movement corresponds to one of at least one next motion state which is able to be derived from a current motion state.

The method may further include storing pre-defined sensing signal patterns of the plurality sensors in association with movements of the body part, wherein the determining of movement of a body part comprises detecting a similarity level by comparing information on the received sensing signals and the stored sensing signal patterns.

The method may further include storing a motion state table that comprises at least one momentary motion state and transition of the at least one momentary motion state.

The method may further include detecting a current motion and determining, based on the motion sate table, at least one next motion state which is able to be transitioned from a current motion state associated with the detected current motion.

The method may further include measuring, at an inertial sensor, an angular velocity and acceleration of movement of the body part.

A wearable device according to an embodiment of the present invention may detect a physical change in human body epidermis so as to recognize movement of a body part and input information based on the movement.

A wearable device according to an embodiment of the present invention may detect a physical change in wrist epidermis, which is caused by a change in wrist muscles, so as to recognize movement of a finger and a wrist.

A wearable device according to an embodiment of the present invention may control an external device based on recognized movement of a body part.

A wearable device according to an embodiment of the present invention may detect a current motion and a next motion by detecting a physical change in epidermis, and control an external device based on the detected current and next motions.

A wearable device according to an embodiment of the present invention may detect a physical change in wrist epidermis, which is caused by a change in wrist muscles, so as to recognize current and a next motion of a finger and a wrist.

DESCRIPTION OF EXEMPLARY EMBODIMENTS

Figure 1:
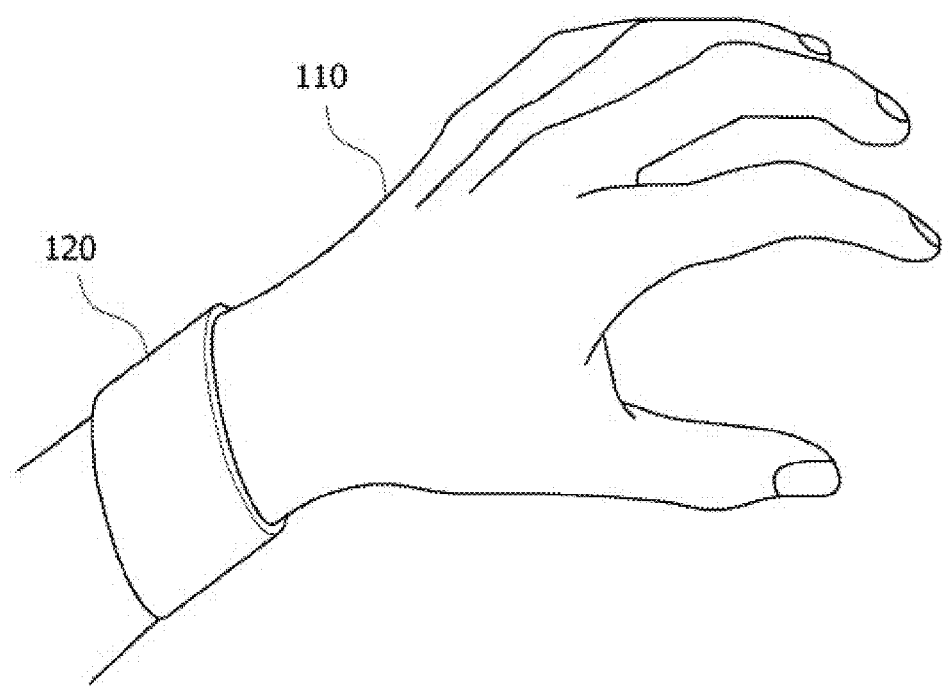
FIG. 1 is a diagram illustrating an example of a wearable device according to an embodiment of the present invention.

Explanation of the present invention is merely embodiments for structural or functional description, so the scope of the present invention should not be construed to be limited to the embodiments explained in the embodiment. That is, since the embodiments may be implemented in several forms, it should also be understood that the scope of the present invention includes equivalents able to realize its technical idea. In addition, it does not mean that a specific embodiment embraces all the purposes or effects suggested in the present invention or embraces only such effects, and therefore, it should be understood that the scope of the present invention is not limited thereto.

Meanwhile, terms used in the following description need to be understood as below.

Terms such as 'first', 'second', etc., may be used to describe various components, but the components are not to be construed as being limited to the terms. The terms are used only to distinguish one component from another component. For example, the 'first' component may be named the 'second' component and the 'second' component may also be similarly named the 'first' component, without departing from the scope of the present invention.

It is to be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "coupled directly to" another element, it may be connected to or coupled to another element without the other element intervening therebetween. Other expressions describing a relationship between components, that is, "between", "directly between", "neighboring to", "directly neighboring to" and the like, should be similarly interpreted.

Terms used in the present specification are used only in order to describe specific exemplary embodiments rather than limiting the present invention. Singular forms are intended to include plural forms unless the context clearly indicates otherwise. It will be further understood that the terms "comprises" or "have" used in this specification, specify the presence of stated features, steps, numerals, operations, components, parts, or a combination thereof, but do not preclude the presence or addition of one or more other features, numerals, steps, operations, components, parts, or a combination thereof.

Indication references of steps (i.e., a, b, and c) are used for convenience of explanation and do not indicate a sequence of the steps. Unless explicitly defined as a specific sequence in the context, the indication references may be performed in a different order. That is, each step can be substantially performed at the same time or can be performed in reverse order in accordance with a function corresponding to the block.

The present invention as described above may be implemented as code that can be written on a computer-readable medium in which a program is recorded and thus read by a computer. The computer-readable medium includes all kinds of recording devices in which data is stored in a computer-readable manner. Examples of the computer-readable recording medium may include a read only memory (ROM), a random access memory (RAM), a compact disk read only memory (CD-ROM), a magnetic tape, a floppy disc, and an optical data storage device. In addition, the computer-readable medium may be implemented as a carrier wave (e.g., data transmission over the Internet). In addition, the computer-readable recording medium may be distributed in a computer system connected via the Internet, and store and implement a computer-readable code in a distributed manner.

Unless indicated otherwise, it is to be understood that all the terms used in the specification including technical and scientific terms have the same meaning as those that are understood by those who skilled in the art. It must be understood that the terms defined by the dictionary are identical with the meanings within the context of the related art, and they should not be ideally or excessively formally defined unless the context clearly dictates otherwise.

FIG. 1 is a diagram illustrating an example of a wearable device according to an embodiment of the present invention.

Referring to FIG. 1, a user is able to input information about a motion by wearing a wearable device 120 on his body 110. Accordingly, the wearable device 120 may control operations of an external device based on input information about the motion. For example, the wearable device 120 shown in FIG. 1 may be in the form of band or bracelet using a flexible sensor array, and may be worn around a wrist of the user and receive information about a motion based on movement of the user's hand.

That is, the user may wear the wearable device 120 around a wrist, and input desired information by moving the hand on which the wearable device 120 is worn. The wearable device 120 may detect a physical change in wrist epidermis, which is caused by movement of the user, and may receive the user's desired information by recognizing a motion based on the detected physical change.

FIG. 1 illustrates an example in which a user wears a wearable device around a wrist, but the present invention can be worn on or attached to a body part other than a wrist to input information. In this case, the wearable device may take a different form to be easily worn on or attached to the different body part.

Figure 2:
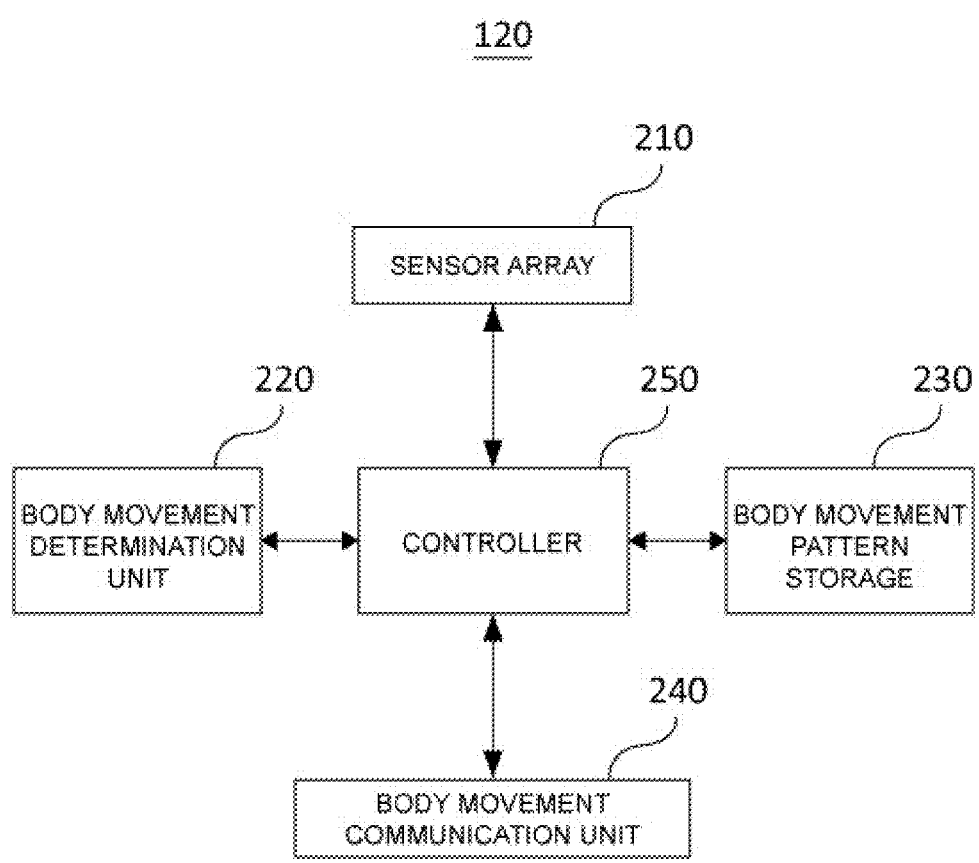
FIG. 2 is a block diagram illustrating configuration of the wearable device of FIG.

FIG. 2 is a block diagram illustrating configuration of the wearable device of FIG. 1.

Referring to FIG. 2, the wearable device 120 includes a sensor array 210, a body movement determination unit 220, a body movement pattern storage 230, a communication unit 240, and a controller 250.

The sensor array 210 detects a physical change in the epidermis of a body area in contact with a plurality of sensors. The sensor array 210 may converts the physical change in the epidermis into an electrical signal and output the electrical signal, and may be disposed in a direction facing the body area so as to easily detect the physical change in the epidermis. The sensor array 210 may include a plurality of non-uniformly arranged sensors and detect strain in the epidermis. In one embodiment, a density of a plurality of sensors may be proportional to a density of muscles underneath the epidermis of a corresponding body area. For example, a plurality of sensors may be densely positioned underneath the epidermis of a body area where muscles are densely positioned, and a plurality of sensors may not be densely positioned underneath the epidermis of a body area where muscles are not densely positioned.

In one embodiment, the sensor array 210 may be in the form of a flexible tactile sensor array to detect strain in the epidermis.

The body movement pattern storage 230 stores movements of body parts in association with pre-defined sensing signal patterns of a plurality of sensors included in the sensor array 210. Information about a sensing signal pattern and movement of a corresponding body part may be defined by a developer and pre-stored in the body movement pattern storage 230. If more information is defined, the wearable device 120 may recognize various movements and receive inputs of various kinds of information based on the movements.

The body movement determination unit 220 may determine movement of a body part based on sensing signals received from the plurality of sensors included in the sensor array 210. In one embodiment, the body movement determination unit 220 may compare detected sensing signals from the sensor array 210 with the sensing signal patterns stored in the body movement pattern storage 230 to find out a matching pattern. In one embodiment, the body movement determination unit 220 may compare sensing signals from the plurality of sensors with the sensing signal patterns to detect a similarity level. The similarity level may correspond to how the received sensing signals and the pre-defined sensing signal patterns are similar, that is, whether the received sensing signals match a specific sensing signal pattern within a predetermined margin of error.

In one embodiment, the body movement determination unit 220 searches for a sensing signal pattern which matches the received sensing signals within the predetermined margin error. If there is a matching pattern, the body movement determination unit 220 recognizes movement of a body part corresponding to the matching pattern. If there is no matching pattern, the body movement determination unit 220 discards the sensing signals sensed by the sensor array 210 and waits again.

The communication unit 240 transmits information about movement of a body part, the movement which is determined by the body movement determination unit 220, to an external device via a communication network. For example, the communication unit 240 may transmit information to an external device linked to the wearable device 120 via the communication network. In doing so, the wearable device 120 may control the external device or input information to the external device.

In one embodiment, the wearable device 120 may include a power unit. The power unit may provide power required for operations of the wearable device 120. For example, the power unit may be a battery, and may be replaceable or rechargeable. The rechargeable-type power unit may be charged using a wired charging means or a wireless charging means.

The controller 250 may control operations and data flows of the sensor array 210, the body movement determination unit 220, the body movement pattern storage 230, and the communication unit 240.

Figure 3:
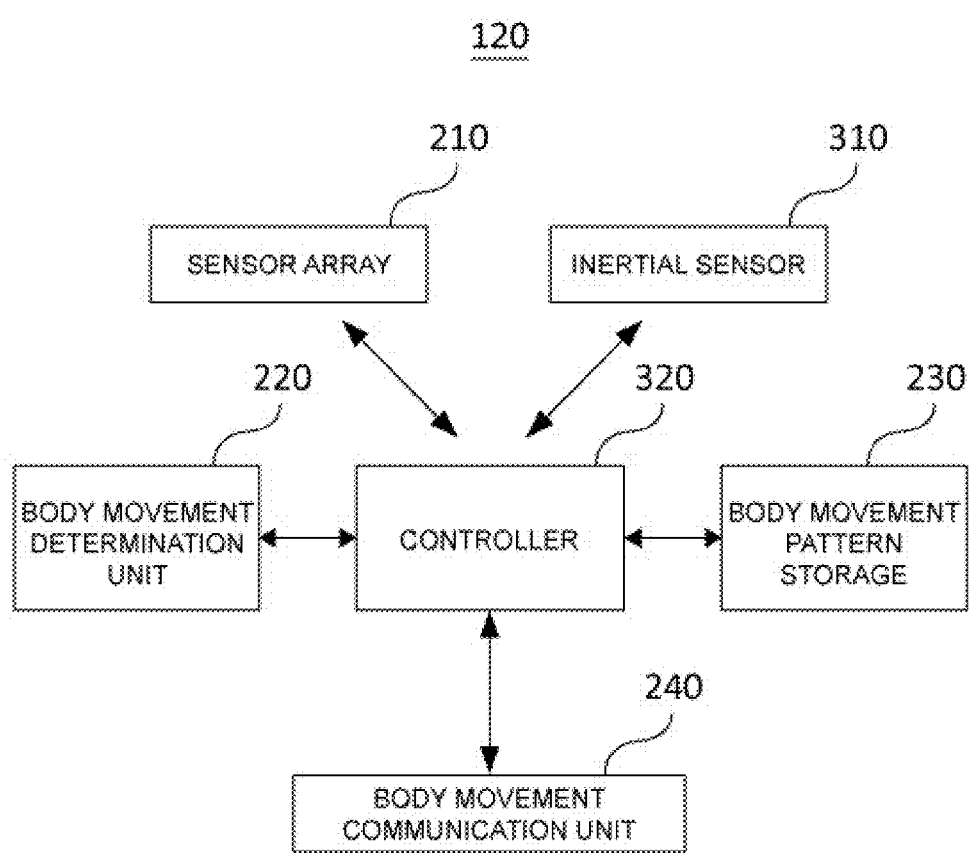
FIG. 3 is a block diagram illustrating configuration of a wearable device according to an embodiment of the present invention.

FIG. 3 is a block diagram illustrating configuration of a wearable device according to an embodiment of the present invention.

Referring to FIG. 3, a wearable device 120 includes an inertial sensor 310, a sensor array 210, a body movement determination unit 220, a body movement pattern storage 230, a communication unit 240, and a controller 320. The following description focuses mainly about differences from the configuration of FIG. 2.

The inertial sensor 310 measures acceleration and angular velocity of movement of a body part, and outputs an electrical signal. In one embodiment, the inertial sensor 310 may be included in the wearable device 120, or may be provided in an external device attached to or possessed by a user.

In one embodiment, if the inertial sensor 310 is included in the wearable device 120, the inertial sensor 310 may be disposed in proximity to an epidermal area underneath a corresponding body part, the epidermal area in which a density of muscles is equal to or less than a specific reference value.

The sensor array 210 detects a physical change in the epidermis of a contacting body part, converts the physical change into an electrical signal, and outputs the electrical signal.

The body movement pattern storage 230 may store pre-defined physical changes, pre-defined inertial patterns, and information about body movements corresponding to the patterns.

The body movement determination unit 220 may search for a matching pattern by comparing an electrical signal (acceleration and angular velocity information), which is output from the inertial sensor 310, and a signal indicating a physical change in the epidermis, which is output from the sensor array 210, with physical changes and inertial patterns which are stored in the body movement pattern storage 230. In one embodiment, the body movement determination unit 220 searches for a pattern which matches within a predetermined margin of error. If there is a matching pattern, the body movement determination unit 220 recognizes a body movement corresponding to the matching pattern as a user's movement.

For example, if a user is grabbing an object while wearing the wearable device 120, the body movement determination unit 220 may recognize the grabbing movement based on sensing signals received from the sensor array 120, the signals which are indicative of a physical change in the epidermis of the corresponding body area, and the body movement determination unit 220 may recognize pulling movement and a pulling direction based on an electrical signal output from the inertial sensor 310.

The wearable device 120 transmits the recognized information to an external device via the communication unit 240 to control the external device or input information to the externa device. For example, if the wearable device 120 is linked to a robot arm (an external device) and recognizes grab-and-pull movement, the wearable device 120 transmits the recognized information to the robot arm so as to control the robot arm to grab and pull an actual object. Alternatively, if the wearable device 120 is linked to a computer (an external device) and recognizes grab-and-pull movement, the wearable device 120 transmits the recognized information to the computer so as to input an command of moving a screen or remove specific information.

The controller 320 controls operations and data flow of the inertial sensor 310, the sensor array 210, the body movement determination unit 220, the body movement pattern storage 230, and the communication unit 240.

Figure 4:
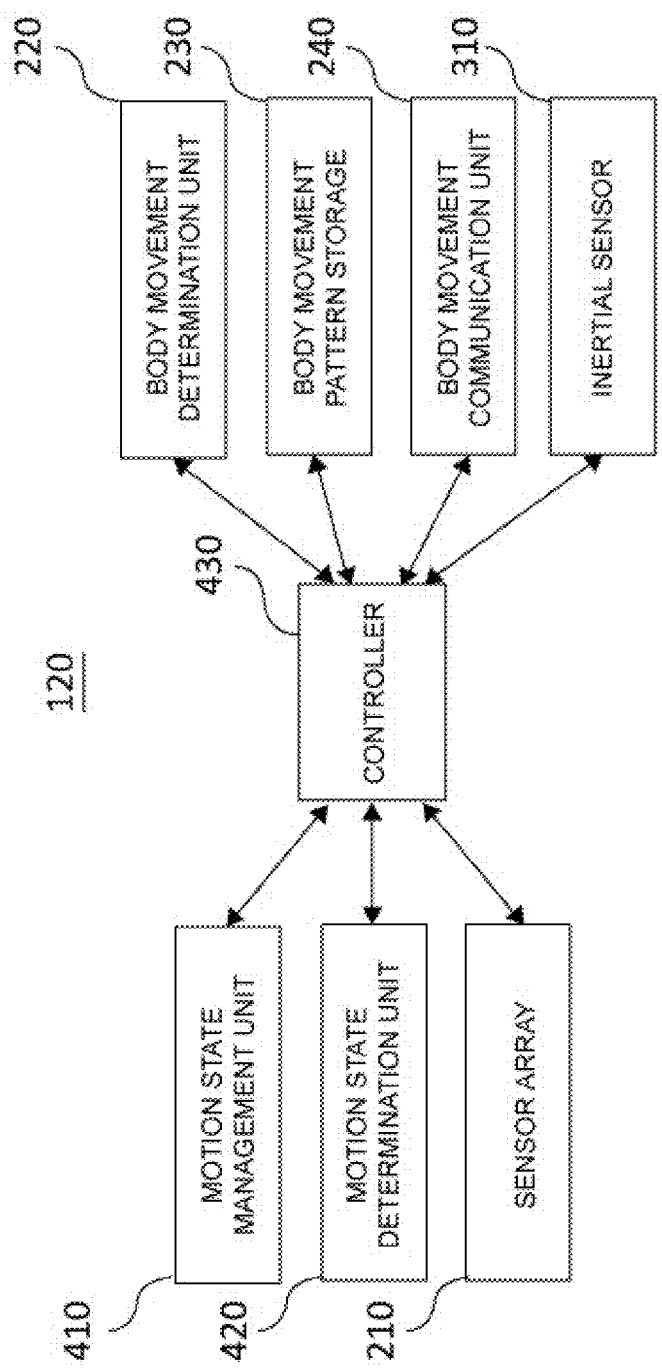
FIG. 4 is a block diagram illustrating configuration of a wearable device according to another embodiment of the present invention.

FIG. 4 is a block diagram illustrating configuration of a wearable device according to another embodiment of the present invention.

Referring to FIG. 4, a wearable device 120 includes a motion state management unit 410, a motion state determination unit 420, a sensor array 210, a body movement determination unit 220, a body movement pattern storage 230, a communication unit 240, an inertial sensor 310, and a controller 430. The following description focuses mainly on differences from the configuration of FIG. 3.

The motion state management unit 410 stores and manages a motion state table, which includes at least one momentary motion state and transition of at least one momentary motion state. A momentary motion state corresponds to a motion recognized at a specific moment, and transition of a momentary motion state means change of the momentary motion state. In one embodiment, a motion state may correspond to at least one momentary motion state or a collection of associated momentary motion states which are continuously recognized from the at least one momentary motion state. With the use of a Finite Statue Machine (FSM) technique, motion states from the motion state table may be managed such that the motion states are classified into an initial motion stage, a motion stage, and a complete motion stage. The initial motion stage, the motion stage, and the complete motion stage are not essential components of a motion state table, and the motion state table may be managed such that motion states are classified into an initial motion stage and a complete motion stage.

For example, in the case where a motion state table is managed by classifying motion states into an initial motion stage, a motion stage, and a complete motion stage, and then an initial motion, an intermediate motion, and a complete motion respectively corresponding to the initial motion stage, the motion stage, and the complete motion stage correspond to Motion1-Motion2-Motion3, Motion1-Motion2-Motion4, and Motion1-Motion3-Motion4, each motion may be stored in association with others, as below in [Table 1].

TABLE 1

| Initial Motion | Intermediate Motion | Complete Motion |
|---|---|---|
| Motion 1 | Motion 2 | Motion 3 |
|  |  | Motion 4 |
|  | Motion 3 | Motion 4 |

In one embodiment, the motion state management unit 410 may store information about operations of an external device in association with corresponding motion states in a motion state table. In the case of operations respectively corresponding to the initial motion stage, the motion stage, and the complete motion stage are continuously performed by a user, it is possible to execute a specific operation of a specific external device and store its relevant information in association with motions, as below in [Table 2].

TABLE 2

| Initial Motion | Intermediate Motion | Complete Motion | Device | Operation of Device |
|---|---|---|---|---|
| Motion 1 | Motion 2 | Motion 3 | Device 1 | Operation A |
|  |  | Motion 4 | Device 2 | Operation B |
|  | Motion 3 | Motion 4 | Device 3 | Operation C |

In one embodiment, a motion state table and a specific operation of the specific external device corresponding to the motion state table may be periodically updated or may be set and stored by a user.

The motion state determination unit 420 may detect the current motion of the user. In one embodiment, the motion state determination unit 420 may determine a state of the current motion by detecting a physical change in the epidermis of a body part 110 in contact with the wearable device 120. How to determine a motion state by detecting a physical change in the epidermis will be described later with reference to FIGS. 5, 7, and 8.

Based on the motion state table, the motion state determination unit 420 may determine at least one next motion state which is associated with the current motion detected by the motion state determination unit 42 and which is able to be transitioned from the current motion. For example, in the case where the current motion determined by the motion state determination unit 420 is Motion1, the next motion state may be determined to be Motion2 and Motion3 with reference to [Table 1]. In one embodiment, in the case where the current motion state is not included in the motion state table, the motion state determination unit 420 may detect a current motion again using the motion state determination unit 420.

The sensor array 210 detects a physical change in the epidermis of a contact body part, converts the physical change into an electrical signal, and outputs the electrical signal. The body movement determination unit 220 determines movement of the body part based on sensing signals from a plurality of sensors included in the sensor array 210, and then determines whether the determined movement of the body part corresponds to one of at least one next motion state which is able to be derived from the current motion state detected by the motion state determination unit 420.

In one embodiment, the body movement determination unit 220 may detect a next motion based on the current motion, and check whether the detected next motion matches at least one next motion state determined by the motion state determination unit 420. In one embodiment, the body movement determination unit 220 may check whether a detected next motion matches at least one determined next motion state within a predetermined margin of error. In one embodiment, how to detect a next motion may be the same as how the motion state determination unit 420 detects the current motion, and it will be described later with references to FIGS. 5, 6, and 7.

For example, referring to [Table 1], if the current motion detected by the motion state determination unit 420 is Motion 1, if Motions 2 and 3 associated with Motion 1 are determined to be next motions which are able to be transitioned from the current motion state, and if a next motion detected by the body movement determination unit 220 is Motion 3, it may be the case where the detected next motion and at least one next motion state determined by the motion state determination unit 420 matches each other.

In another example, if a next motion detected by the body movement determination unit 220 is Motion4, it may be the case where the detected next motion does not match at least one next motion state determined by the motion state determination unit 420, and therefore, the body movement determination unit 220 may detect a next motion again. That is, the next motion determined by the motion state determination unit 420 to be possibly transitioned from the current motion state corresponds to Motions 2 and 3, but the next motion detected by the body movement determination unit 220 is Motion 4, and therefore, the detection results do not match each other.

In one embodiment, if a motion state table is divided by an initial motion and a complete motion stage, the motion state determination unit 420 may detect the current motion corresponding to the initial motion stage, and the body movement determination unit 220 may detect a next motion corresponding to the complete motion stage.

In one embodiment, if a motion state table is divided by an initial motion stage, a motion stage, and a complete motion stage, the motion state determination unit 420 may detect an initial motion corresponding to the initial motion stage, and determine at least one intermediate motion associated with the initial motion. The body movement determination unit 220 may detect an intermediate motion corresponding to the motion stage, and check whether the detected intermediate motion matches at least one intermediate motion determined by the motion state determination unit 420. Then, if the intermediate motion detected by the body movement determination unit 220 matches at least one intermediate motion determined by the motion state determination unit 420, the motion state determination unit 420 may determine at least one complete motion associated with the intermediate motion. The body movement determination unit 220 may detect a complete motion corresponding to the complete motion stage, and check whether the detected complete motion matches at least one complete motion determined by the motion state determination unit 420. Then, if the complete motion detected by the body movement determination unit 220 matches at least one complete motion determined by the motion state determination unit 420, the initial motion, the intermediate motion, and the complete motion from the motion state table are all found matching, and therefore, the communication unit 240 may transmit information about an operation to an external device associated with the corresponding motion.

For example, how to detect Motion1-Motion2-Motion3 respectively corresponding to an initial motion stage, a motion stage, and a complete motion stage is described with reference to [Table 1]. 1) The motion state determination unit 420 detects Motion1 as the current motion (the initial motion stage, that is, an initial stage), the motion state determination unit 420 determines Motions 2 and 3 as next motions (the motion stage, that is, an intermediate motion), and the body movement determination unit 220 detects Motion2 as a next motion (intermediate motion). In such a case, 2) if the motion state determination unit 420 may determine Motions 3 and 4 as a next-next motion (a complete motion stage, that is, a complete motion) associated with Motion2, which is the next motion (intermediate motion), and the body movement determination unit 220 detects Motion3 as a next-next motion (complete motion), the detected next-next motion (complete motion) and at least one next-next motion determined by the motion state determination unit 420 may match to Motion 3.

In one embodiment, if a motion state table manages motions classified into an initial motion stage and a complete motion stage and into an initial motion stage, a motion stage, and a complete motion stage, the motion state table may be managed as below in [Table 3].

TABLE 3

| Initial Motion | Initial Motion | Complete Motion | Device | Operation of Device |
|---|---|---|---|---|
| Motion 1 | Motion 2 | — | Device 1 | Operation A |
|  |  | Motion 3 | Device 2 | Operation B |
|  |  | Motion 4 | Device 3 | Operation C |
|  | Motion 3 | — | Device 4 | Operation D |
|  |  | Motion 4 | Device 5 | Operation E |
|  | — | — | Device 6 | Operation F |

In one embodiment, if the current motion (an initial motion) is determined by the motion state determination unit 420 and at least one next motion (intermediate motion) state determined by the motion state determination unit 420 includes '-', which means there is no next motion (intermediate motion), it may be possible to determine that there is no next motion (intermediate motion) unless a next motion (intermediate motion) is not detected by the body movement determination unit 220 for a predetermined period of time.

For example, with reference to [Table 3], if Motion1 is detected by the motion state determination unit 420 as an initial motion and if at least one next motion (intermediate motion) determined by the motion state determination unit 420 to be associated with the initial motion includes '-', which means there is no next motion (intermediate motion), it is possible to determine that there is no next motion (intermediate motion) unless a next motion (intermediate motion) is detected by the body movement determination unit 220 for a predetermined period of time and it is possible to determine that there is even no next-next motion (complete motion). That is, Device 1 may be controlled only by Motion1 to perform Operation A.

If a next motion (intermediate motion) is detected by the body movement determination unit 220, if the detected next motion (intermediate motion) matches at least one next motion state determined by the motion state determination unit 420, and if the at least one next-next motion (complete motion) state determined by the motion state determination unit 420 to be associated with the next motion (intermediate motion) includes '-', which means there is no next-next motion (complete motion), it is possible to determine that there is no next-next motion (complete motion) unless a next-next motion (complete motion) is not detected by the body movement determination unit 220 for a predetermined period of time.

For example, with reference to [Table 3], Motion1 is detected by the motion state determination unit 420 as the current motion (initial motion), Motion 3 is detected by the body movement determination unit 220 as a next motion (intermediate motion), and at least one next motion (intermediate motion) determined by the motion state determination unit 420 matches the detected next motion (intermediate motion) to be Motion3. In this case, if a state of a next-next motion (complete motion) associated with a next motion (intermediate motion) is determined by the motion state determination unit 420 to be '-' and Motion 4 and any next-next motion (complete motion) is not detected by the body movement determination unit 220 for a predetermined period of time, the next-next motion (complete motion) is determined to be '-'. That is, Device 4 may be controlled only by Motions 1 and 3 to perform Operation D.

The body movement pattern storage 230 may store pre-defined physical changes, pre-defined inertial patterns, and information on body movements corresponding to the patterns.

In the case where at least one next motion state determined by the motion state determination unit 420 matches a next motion detected by the body movement determination unit 220, the communication unit 240 may transmit, via the motion state management unit 410, information to an external device the information about operations of the external device, the information which is associated with a corresponding motion state table. For example, with reference to [Table 3], if Motion1-Motion2-Motion4 is determined by the motion state determination unit 420 and the body movement determination unit 220, the communication unit 240 may transmit information on Device 3-Operation C, which is associated with a motion state table corresponding to Motion1-Motion2-Motion4, to Device 3 so that Device 3 may perform Operation C.

The inertial sensor 310 measures acceleration and angular velocity of movement of a body part, and outputs an electrical signal. In one embodiment, the inertial sensor 310 may be included in the wearable device 10, or may be provided in another device worn on or possessed by a user.

In one embodiment, if the inertial sensor 310 is included in the wearable device 120, the inertial sensor 310 may be positioned in proximity to an epidermal region underneath a corresponding body area, the epidermal region in which a density of muscles is equal to or less than a specific reference value.

In one embodiment, the motion state determination unit 420 may detect a current motion based on an electrical signal (acceleration and angular velocity information) output from the inertial sensor 310 and sensing signals, including a signal indicative of a physical change in the epidermis, output from the sensor array 310. The body movement determination unit 220 may determine whether a determined movement of a body part corresponds to one of at least one next motion state which is able to be derived from the current motion state.

For example, if a user is grabbing an object while wearing the wearable device 120, the body movement determination unit 220 may recognize the grabbing movement based on sensing signals received from the sensor array 120, the signals which are indicative of a physical change in the epidermis of a corresponding body area, and the body movement determination unit 220 may recognize pulling movement and a pulling direction based on an electrical signal output from the inertial sensor 310.

The controller 430 controls operations and data flows of the motion state management unit 410, the motion state determination unit 420, the sensor array 210, the body movement determination unit 220, the body movement pattern storage 230, the communication unit 240, and the inertial sensor 310.

Figure 5:
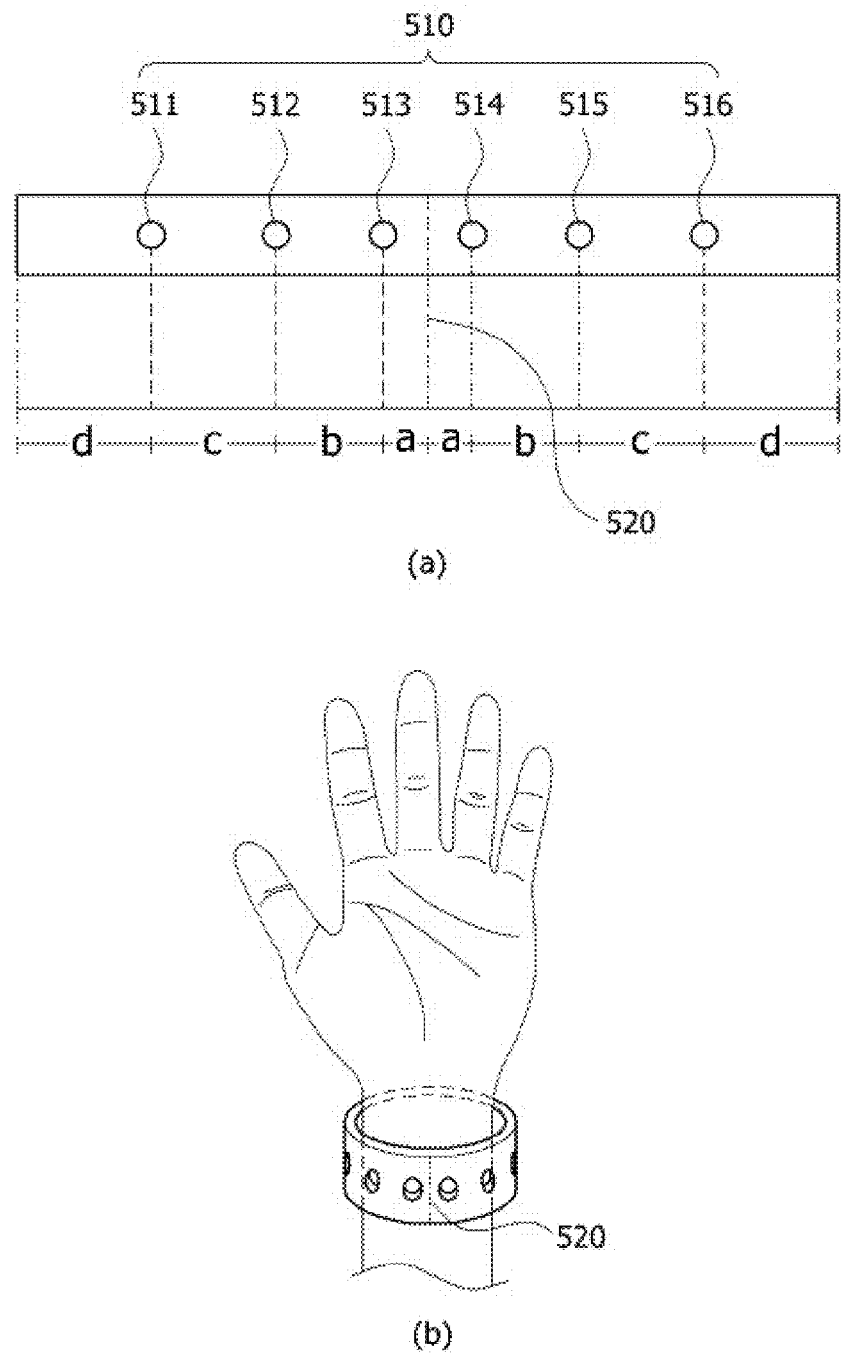
FIG. 5 is a diagram illustrating an example of a sensor array shown in FIG. 2.

FIG. 5 is a diagram illustrating an example of a sensor array shown in FIG. 2, FIG. 3, or FIG. 4.

Referring to (a) of FIG. 5, the sensor array 210 may include a plurality of sensors 510. The plurality of sensors 510 may include a first sensor 511, a second sensor 512, a third sensor 513, a fourth sensor 514, a fifth sensor 515, and a sixth sensor 516, and may detect a physical change in the epidermis of a contact body area.

In one embodiment, in the case where the sensor array 210 is worn around a wrist, as shown in (b) of FIG. 3, and a center line 520 of the sensor array 210 is positioned in the intrinsic muscles of the wrist, the plurality of sensors 510 is arranged at distances a, b, c, and d from each other based on a density of muscles in the wrist. That is, if the wearable device 120 is worn around a wrist, a density of the plurality of sensors in the intrinsic muscles of the wrist may different from a density of the plurality of sensors in the extrinsic muscles of the wrist. For example, wrist muscles are relatively more densely positioned in the intrinsic muscles of the wrist and relatively less densely positioned in the extrinsic muscles of the wrist, and therefore, the plurality of sensors 510 may be arranged at distances corresponding to a<b<c<d. That is, a density of a plurality of sensors 510 in the intrinsic muscles of the wrist may be greater than a density of a plurality of sensors 510 in the extrinsic muscles of the wrist. In addition, depending on a type of a contact body part or the position of muscles underneath the contact body part, the plurality of sensors 510 may be arranged in a different manner by which a physical change in epidermis of a body region can be detected efficiently.

In (a) of FIG. 3, each of the plurality of sensors 510 on the sensor array 210 may detect a strain in the epidermis of a contact body part. For example, in the case of the wearable device 120 shown in FIG. 1, the sensor array 210 may detect a fine strain in the wrist epidermis, which is caused by wrist muscles.

Figure 7:
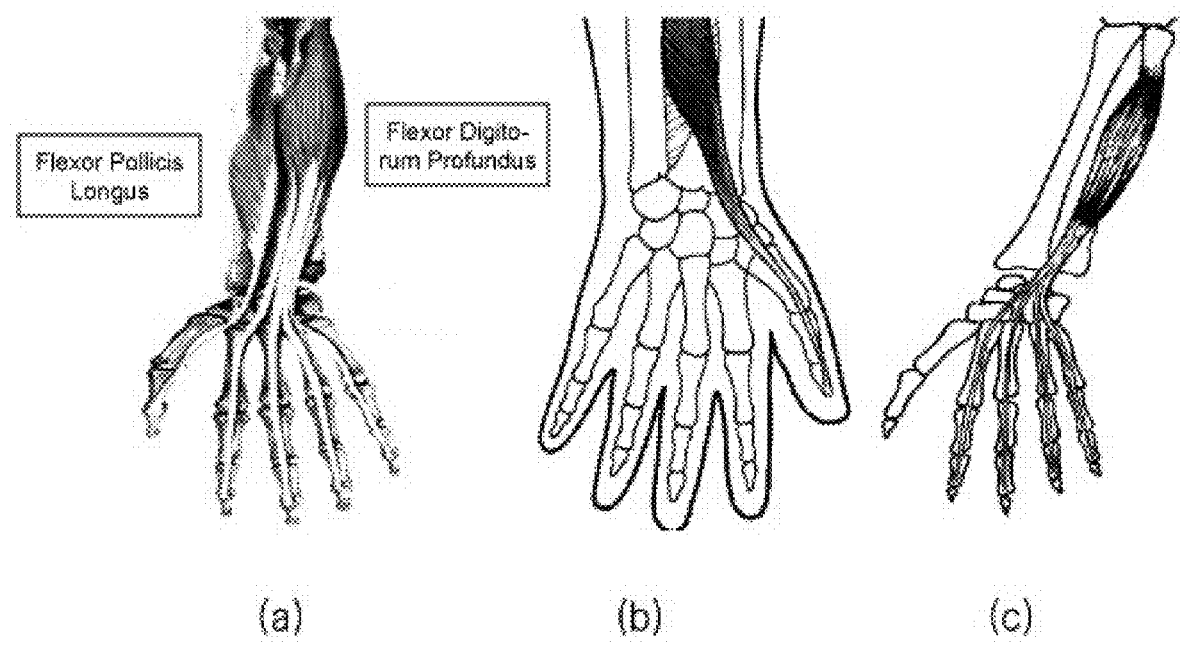
FIG. 7 is a diagram illustrating finger and wrist muscles.

For example, with reference to finger and wrist muscles shown in FIG. 7, a person moves his hand (for example, a finger and/or a wrist) by moving the flexor pollicis longus and the flexor digitorum profundus which penetrate a wrist. That is, movement of a hand is changed by movement of the flexor pollicis longus and the flexor digitorum profundus, and the wrist epidermis in which the flexor pollicis longus and the flexor digitorum profundus are located is changed by movement of flexor pollicis longus and the flexor digitorum profundus. In FIG. 7, (a) shows finger and wrist muscles, FIG. 7, (b) shows the flexor pollicis longus, and (c) shows the flexor digitorum profundus.

In the case where the sensor array 210 is positioned in a wrist, the sensor array 210 detects a strain in the epidermis caused by movement of the flexor pollicis longus and the flexor digitorum profundus, and converts the strain into an electrical signal. The motion state determination unit 220 and the body movement determination unit 240 compares a sensing signal from the sensor array 210 with pre-stored sensing signal patterns. If there is a matching pattern, the motion state determination unit 220 and the body movement determination unit 240 recognizes movement corresponding to the matching sensing signal pattern as hand movement of the user and detect the current and next motion based on the movement.

In one embodiments, the body movement pattern storage 230 may store and manage sensing signal patterns which are pre-defined based on sensing signals respectively sensed by the plurality of sensors 510. More specifically, sensing signal patterns may be defined based on whether each of the first sensor 511, the second sensor 512, the third sensor 513, the fourth sensor 514, the fifth sensor 515, and the sixth sensor 516 detects a physical change in the epidermis of a corresponding contact body part is determined, and based on a degree of strain of the epidermis if such a physical change is detected. For example, referring to [Table 4], sensing signal patterns corresponding to {(first sensor, yes), (second sensor, yes), (third sensor, no), (fourth sensor, no), (fifth sensor, no), (sixth sensor, yes)} may be stored in association with movement of clenching a fist. If a sensing signal received from the plurality of sensors 510 included in the sensor array 210 corresponds to {(first sensor, yes), (second sensor, yes), (third sensor, no), (fourth sensor, no), (fifth sensor, no), (sixth sensor, yes)}, it may be recognized that a user wearing the wearable device 120 is clenching a fist.

TABLE 4

| | First Sensor | Second Sensor | Third Sensor | Fourth Sensor | Fifth Sensor | Sixth Sensor | Movement |
|---|---|---|---|---|---|---|---|
| Detection of Physical Change | Yes | Yes | No | No | No | Yes | Clenching Fist |
| | Yes | No | Yes | Yes | No | Yes | Moving Wrist Upward and Downward |
| | No | No | Yes | Yes | No | No | Twisting Wrist |

Figure 6:
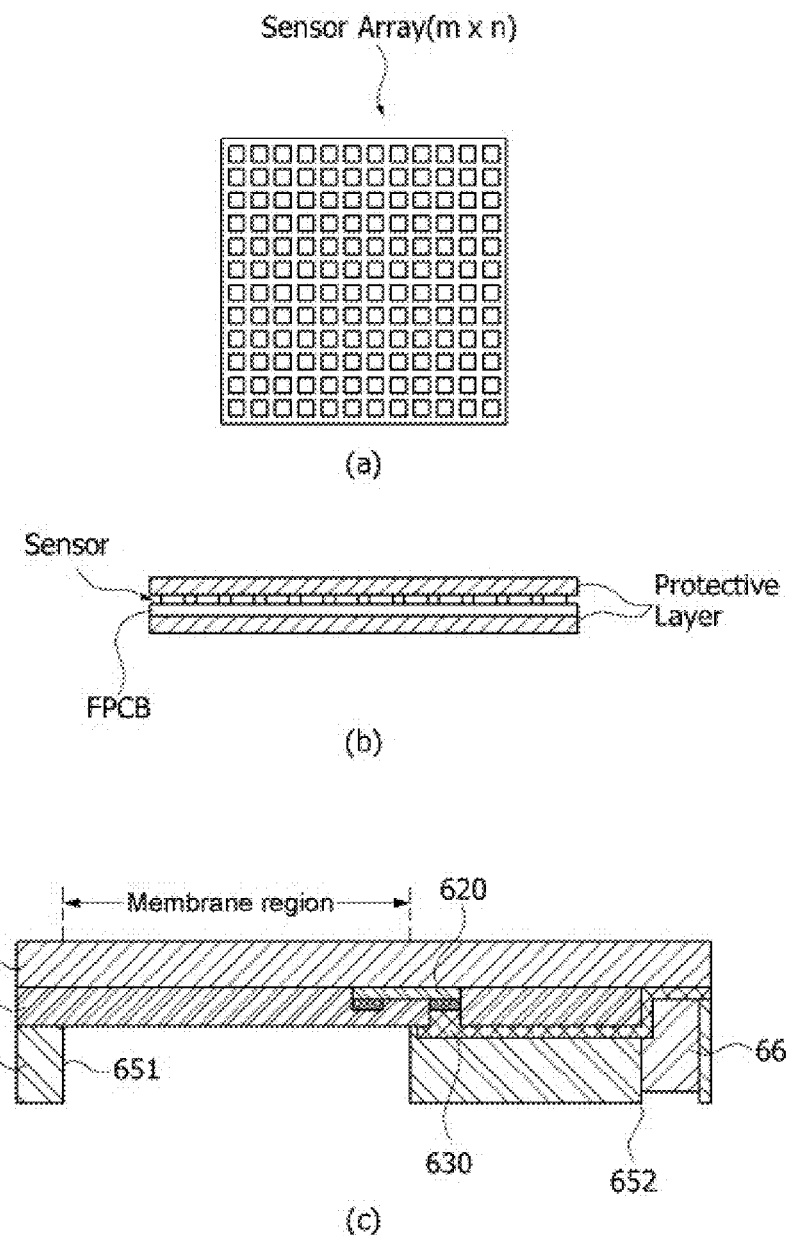
FIG. 6 is a diagram illustrating an example of a sensor included in the sensor array shown in FIG. 3.

FIG. 6 is a diagram illustrating an example of a sensor included in the sensor array of FIG. 3.

Each of the plurality of sensors 510 included in the sensor array 210 may be configured as in (a) of FIG. 4 or (b) of FIG. 4.

Referring to (a) of FIG. 4, each of the plurality of sensors 510 is formed as a plurality of tactile sensor arrays to detect a physical strain in the epidermis in contact with the sensors. A tactile sensor is a sensor configured to detect a physical property of a contact region into an electrical signal, and a silicon-based CMO tactile sensor, a polymer-based tactile sensor, a pressure sensitive material-based tactile sensor, and the like may be used as the sensor. In one embodiment, each of the plurality of sensors 510 may include a flexible printed circuit board (FPCB (in which a plurality of tactile sensors are mounted in array, and polymer projective layers respectively laminated on and underneath the FPCB.

In one embodiment, tactile sensors from the plurality of sensors 510 are arranged as arrays of m×n, but a tactile sensor array may be arranged in a different form by which a physical strain can be detected efficiently according to a type of a contact region.

Referring to FIG. (b) of FIG. 4, each of the plurality of sensors 510 may be configured as a tactile sensor module, and the flexible tactile sensor module may have a flat cable-type terminal connected to an electrode line, and may be manufactured along with tactile sensors. In addition, the tactile sensor module may be implemented as a flexible tactile sensor module having a signal processing connection unit which is in the form of a Flexible Flat Cable (FFC), In one embodiment, the flexible tactile sensor module includes a strain gauge 620, an insulating film 611 and 612, a first electrode line 660, a second electrode lien 630, a first opening 651, a second opening 652, and a supporter 650. More specifically, the flexible tactile sensor module may include: the strain gauge 620; the insulating film 611 and 612 surrounding the strain gauge 620; the first electrode line 660 connected to one end of the strain gauge 620 and formed in the inside and the surface of the insulating film 611 and 612; the second electrode line 630 connected to the other end of the strain gauge 620 and formed in the inside and the surface of the insulating film 611 and 612; the first opening 651 causing a part of the strain gauge 620 to rise; the second opening 652 causing the second electrode line 630 to be exposed; and the support 650 formed below the insulating film 611 and 612.

In one embodiment, the insulating film 611 and 612 may be in a structure such that a first insulating layer 611 and a second insulating layer 612 are separate from each other, that one end of the strain gauge 620 is connected between the first insulating layer 611 and the second insulating layer 612 to be arranged between the first insulating layer 611 and the second insulating layer 612, and that the second electrode line 630 is connected to the other end of the strain gauge 620 inside the second insulating layer 612 to be arranged along the surface of the first insulating layer 611.

In one embodiment, a plated layer covered on the first and second electrode lines 660 and 630 may be further formed inside the second opening 652.

In one embodiment, the insulating film 611 and 612 may be formed of a flexible polymer.

In one embodiment, the sensor array 210 including the plurality of sensors 510 configured as in (a) or (b) of FIG. 4 may detect a strain in the epidermis of a contact body part, and more specifically, the sensor array 210 may detect a strain in the epidermis of a contact body part using the plurality of sensors 510 which include a plurality of tactile sensors arranged as arrays. For example, in the case of the wearable device 120 of FIG. 1, the sensor array 210 may detect a fine strain of the wrist epidermis, which is caused by a change in wrist muscles.

Figure 8:
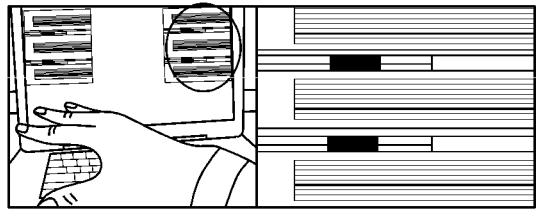
FIG. 8 is a diagram illustrating an exemplary procedure of detecting a change in epidermis using the wearable device of FIG. 1.
Figure 8:
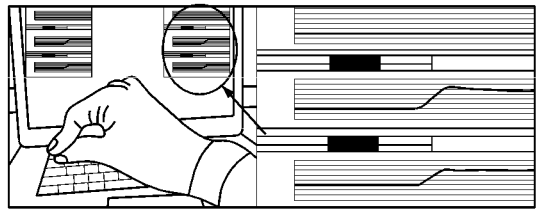
Figure 8:
Figure 8:
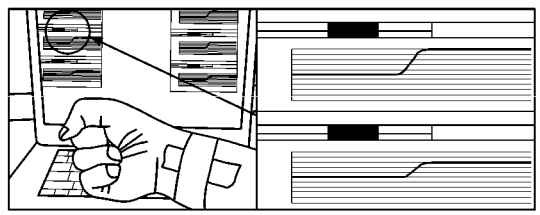
Figure 8:
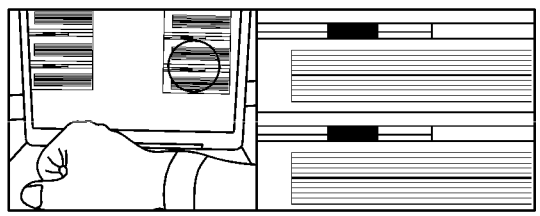
Figure 8:
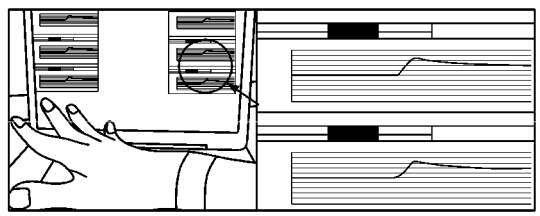
Figure 8:
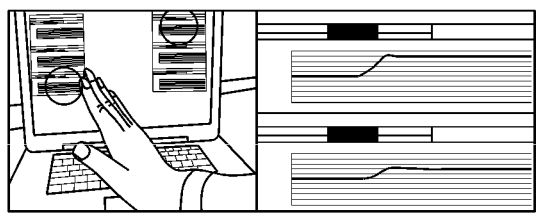
Figure 8:
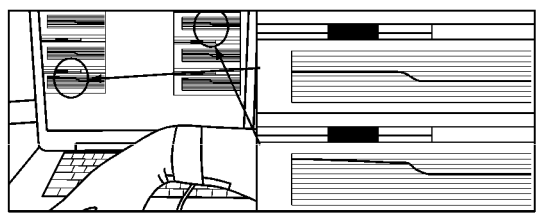

FIG. 8 is a diagram illustrating an exemplary procedure of how to detect a physical change in epidermis using the wearable device of FIG. 1.

Referring to FIG. 8, it is possible to detect a strain in the wrist epidermis using the wearable device 120 before and after movement of a finger or a wrist, and output a signal indicative of the detected strain. In FIG. 6, picking up with fingers, twisting a wrist, spreading a finger, and moving a wrist upward and downward are illustrated as examples of movement. However, the wearable device 120 may detect a strain in the wrist epidermis in response to various movements, and recognize movement of a hand (at least one of a finger and a wrist) based on the detected strain.

For example, referring to FIG. 8, different before-movement sensing signals and after-movement sensing signals are received from the plurality of sensors 510 of the sensor array 210, which is worn around a wrist, according to a type of movement of at least one of a finger and a wrist. In this case, the motion state determination unit 220 and the body movement determination unit 240 compare a sensing signal, received from the sensor array 210, with prestored sensing signal patterns so as to determine a user's hand movement and detect the current motion and a next motion.

Figure 9:
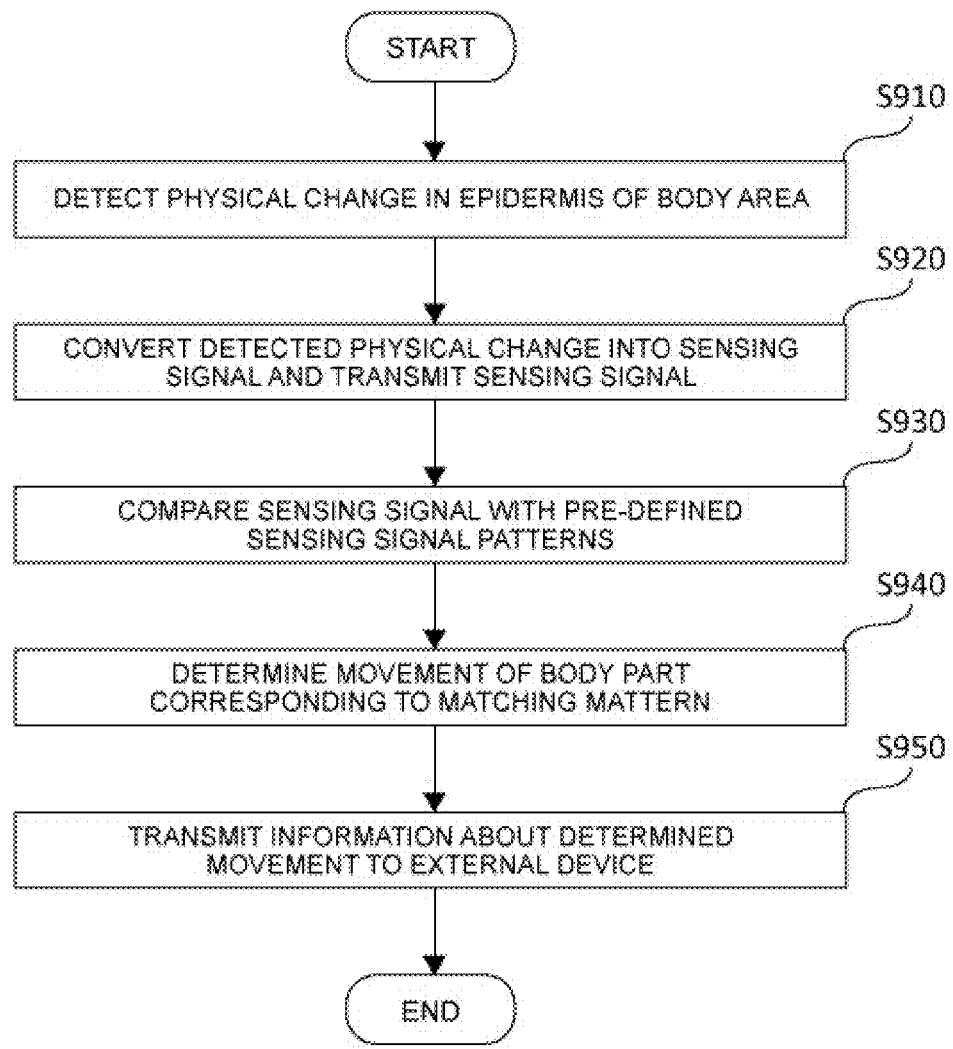
FIG. 9 is a flowchart of a method of inputting information using a wearable device according to an embodiment of the present invention.

FIG. 9 is a flowchart illustrating a method of inputting information using a wearable device according to an embodiment of the present invention.

Referring to FIG. 9, a sensor array 210 detects a physical change in epidermis of a body area in contact with the sensor array 210 (S910). For example, the sensor array 210 may be configured as a plurality of sensors 510 or tactile sensor arrays to detect a strain in the epidermis of the contacting body area. In the case of a wearable device to be worn around a wrist, the sensor array 210 may detect a physical change in the wrist epidermis, which is caused by a change in wrist muscles.

The sensor array 210 converts the physical change, detected by the plurality of sensors 510, into a sensing signal and transmits the sensing signal to a body movement determination unit 220 (S920).

The body movement determination unit 220 compares the sensing signal, received from the sensor array 210, with pre-defined sensing signal patterns stored in the body movement pattern storage 230 to check whether they match (S930). If there is a matching pattern, the body movement determination unit 220 may recognize movement of a body part corresponding to the matching pattern as a user's movement (S940).

In one embodiment, the method of inputting information according to the present invention may further include measuring an angular velocity and acceleration of the movement of the body part using an inertial sensor 310. In this case, the body movement determination unit 220 may recognize the user's movement based on information about a physical change in the epidermis measured by the sensor array 210 and based on the angular velocity and acceleration measured using the inertial sensor 310.

A communication unit 240 may transmit the information about the movement of the body part, the movement which is recognized by the body movement determination unit 220, to an external device via a wired or wireless communication network (S950). For example, the communication unit 240 may transmit information about movement to an external device via a short-ranged wireless communication network, such as Bluetooth and Ultra Wide Band (UWB).

In one embodiment, if a user controls an Internet of Things (IoT) device using a wearable device, the communication unit 240 confirms the IoT device which is linked to the wearable information inputting device via a wireless communication network, and transmit information about movement to the linked IoT device.

Figure 10:
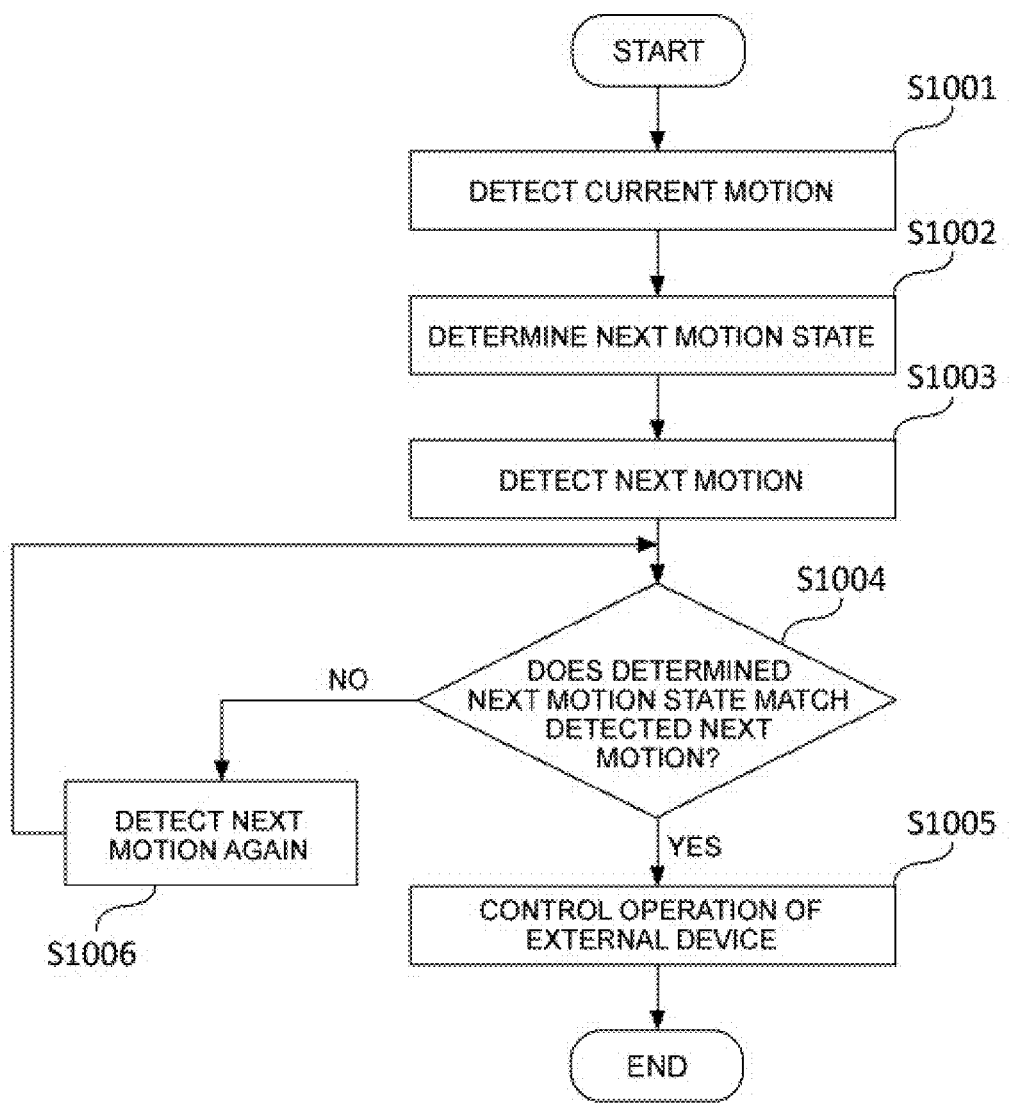
FIG. 10 is a flowchart of a method of inputting information using a wearable device according to another embodiment of the present invention.

FIG. 10 is a flowchart illustrating a method of inputting information using a wearable device according to an embodiment of the present invention.

The motion state determination unit 420 detects the current motion (S1001). In one embodiment, the motion state determination unit 420 may determine the current motion state based on sensing signals from a plurality of sensors included in the sensor array 210, the signals which are indicative of a physical change in the epidermis of a contacting body area.

Based on a motion state table, the motion state determination unit 420 determines at least one next motion state associated with the current motion, which is detected by the motion state determination unit 420 (S1002).

The body movement determination unit 220 detects a next motion (S1003), and checks whether the detected next motion matches at least one next motion state determined by the motion state determination unit 420 (S1004).

If the next motion detected by the body movement determination unit 220 matches the next motion state determined by the motion state determination unit 420, the communication unit 240 transmits corresponding information to a specific external device associated with the corresponding motion state table so as to control operations of the external device to perform a specific operation (S1005).

If the next motion detected by the body movement determination unit 220 does not match the next motion state determined by the motion state determination 420, the body movement determination 220 detects a next motion again (S1006), and returns to the step S1004 to check whether the next motion detected by the body movement determination unit 220 matches the next motion state determined by the motion state determination unit 420.

It is to be understood that while preferable embodiments of the invention are illustrated above, it will be apparent to those skilled in the art that various changes and modifications may be made without departing from the scope of the invention.

What is claimed is:

1. A wearable device comprising:
a sensor array having a plurality of sensors each configured to detect a physical change in epidermis of a corresponding body area;
a motion state management unit configured to store a motion state table including at least one momentary motion state and transition of the at least one momentary motion state, wherein motion states stored in the motion state table are classified into an initial motion stage, a motion stage, and a complete motion stage, the motion state table being associated with information about operations of a plurality of external devices, wherein each operation information of each external device corresponds to a combination of motions detected at the initial motion stage, the motion stage, and the complete motion stage;
a motion state determination unit configured to detect a current motion state belonging to the initial motion stage, and to determine, based on the motion state table, at least one next motion state which is able to be derived from the detected current motion state and which belongs to the motion stage or the complete motion stage;
a body motion determination unit configured to determine a motion of a body part based on sensing signals from the plurality of sensors, to check if the determined motion of the body part matches to the at least one next motion state determined by the motion state determination unit, wherein the body motion determination unit detects a next motion through the sensor array based on a current motion, and checks whether the detected next motion matches the at least one next motion state determined by the motion state determination unit;
an inertial sensor configured to measure an angular velocity and acceleration and configured to be positioned in proximity to an epidermal region, in which a density of muscles is equal to or less than a specific reference value, underneath the corresponding body area; and
a communication unit configured to, when the detected next motion matches the at least one next motion state determined by the motion state determination unit, transmit, via the motion state management unit, an operation information to a specific device among the plurality of external devices, the operation information corresponding to the combination of motions detected at the initial motion stage, the motion stage, and the complete motion stage,
wherein the plurality of sensors are arranged in the sensor array such that a density of the plurality of sensors is proportional to a density of muscles underneath the epidermis of the corresponding body area, and
wherein, when the corresponding body area is a wrist, a density of the plurality of sensors arranged to correspond to intrinsic muscles of the wrist is greater than a density of the plurality of sensors arranged to correspond to extrinsic muscles of the wrist.

2. The wearable device of claim 1, wherein the sensor array is positioned on the wrist to detect a physical change in wrist epidermis, which is caused by a change in muscles including flexor hallucis longus and flexor digitorum profundus.

3. The wearable device of claim 1, further comprising a body movement pattern storage configured to store predefined sensing signal patterns of the plurality of sensors in association with motions of the body part.

4. The wearable device of claim 3, wherein the body motion determination unit detects a similarity level by comparing information on the received sensing signals and the sensing signal patterns stored in the body movement pattern storage, and determines the motion of the body part based on the similarity level.

5. The wearable device of claim 1, wherein, when the detected current motion state is not included in the motion state table, the motion state determination unit detects a current motion again.

6. The wearable device of claim 1, wherein, when the detected next motion does not match the at least one next motion state determined by the motion state determination unit, the body motion determination unit detects a next motion again.

7. The wearable device of claim 1, wherein the body motion determination unit determines the motion of the body part based on the angular velocity and acceleration measured by the inertial sensor along with the sensing signals from the plurality of sensors.

8. A method of inputting information to external devices using a wearable device, the method comprising:
detecting a physical change in epidermis of a corresponding body area from a sensor array, of the wearable device, having a plurality of sensors, wherein the detecting includes positioning an inertial sensor at an epidermal region, in which a density of muscles is equal to or less than a specific reference value, underneath the corresponding body area, and measuring, at the inertial sensor, an angular velocity and acceleration of movement of the body part;
reading, by a controller of the wearable device, a motion state table including at least one momentary motion state and transition of the at least one momentary motion state, wherein motion states stored in the motion state table are classified into an initial motion stage, a motion stage, and a complete motion stage, the motion state table being associated with information about operations of a plurality of external devices, wherein each operation information of each external device corresponds to a combination of motions detected at the initial motion stage, the motion stage, and the complete motion stage;
detecting, by a motion state determination unit of the wearable device, a current motion state belonging to the initial motion stage, and determining, based on the motion sate table, at least one next motion state which is able to be derived from the detected current motion state and which belongs to the motion stage or the complete motion stage;
determining, by a body motion determination unit of the wearable device, a motion of a body part based on sensing signals received from the plurality of sensors, and checking if the determined motion of the body part matches to the at least one next motion state determined by the motion state determination unit;
detecting, by the body motion determination unit of the wearable device, a next motion through the sensor array based on a current motion, and checking whether the detected next motion matches the at least one next motion state determined by the motion state determination unit; and
transmitting, when the detected next motion matches the at least one next motion state determined by the motion state determination unit, via the motion state management unit, an operation information to a specific device among the plurality of external devices, the operation information corresponding to the combination of motions detected at the initial motion stage, the motion stage, and the complete motion stage, wherein the plurality of sensors are arranged in the sensor array such that a density of the plurality of sensors is proportional to a density of muscles underneath the epidermis of the corresponding body area, and wherein, when the corresponding body area is a wrist, a density of the plurality of sensors arranged to correspond to intrinsic muscles of the wrist is greater than a density of the plurality of sensors arranged to correspond to extrinsic muscles of the wrist.

9. The method of claim 8, further comprising storing pre-defined sensing signal patterns of the plurality sensors in association with motions of the body part, wherein the determining of motion of a body part comprises detecting a similarity level by comparing information on the received sensing signals and the stored sensing signal patterns.

* * * * *